United States Patent
Maandi et al.

(10) Patent No.: US 9,176,061 B2
(45) Date of Patent: Nov. 3, 2015

(54) METHODS FOR MEASURING DEGREE OF CURE OR SOLIDIFICATION OF A COMPOSITION

(71) Applicant: Henkel Corporation, Rocky Hill, CT (US)

(72) Inventors: Eerik Maandi, Rocky Hill, CT (US); Alan E. Litke, New Haven, CT (US)

(73) Assignee: Henkel IP & Holding GmbH, Duesseldorf (DE)

( * ) Notice: Subject to any disclaimer, the term of this patent is extended or adjusted under 35 U.S.C. 154(b) by 0 days.

(21) Appl. No.: 13/777,246

(22) Filed: Feb. 26, 2013

(65) Prior Publication Data

US 2013/0171651 A1    Jul. 4, 2013

Related U.S. Application Data

(63) Continuation of application No. PCT/US2011/061600, filed on Nov. 21, 2011.

(60) Provisional application No. 61/416,007, filed on Nov. 22, 2010.

(51) Int. Cl.
| | |
|---|---|
| *B29C 71/04* | (2006.01) |
| *C08F 2/46* | (2006.01) |
| *C08G 61/04* | (2006.01) |
| *G01N 21/64* | (2006.01) |
| *G01N 33/44* | (2006.01) |

(52) U.S. Cl.
CPC ............ *G01N 21/643* (2013.01); *G01N 33/442* (2013.01)

(58) Field of Classification Search
CPC .......................... G01N 33/442; G01N 21/643
USPC .............................. 522/71, 189, 184, 1; 520/1
See application file for complete search history.

(56) References Cited

U.S. PATENT DOCUMENTS

| | | | |
|---|---|---|---|
| 4,885,254 A | | 12/1989 | Sung |
| 5,100,802 A | | 3/1992 | Mickols |
| 5,166,236 A | * | 11/1992 | Alexander et al. ............ 524/111 |
| 5,598,005 A | | 1/1997 | Wang et al. |
| 5,606,171 A | * | 2/1997 | Neckers et al. ............ 250/459.1 |
| 5,707,587 A | | 1/1998 | Blanchard |
| 5,955,002 A | | 9/1999 | Neckers et al. |

OTHER PUBLICATIONS

International Search Report for PCT/US2011/061600, dated May 24, 2012, 2 pages.

* cited by examiner

*Primary Examiner* — Ling Choi
*Assistant Examiner* — Jessica E Whiteley
(74) *Attorney, Agent, or Firm* — Steven C. Bauman

(57) ABSTRACT

The present invention is directed to methods of measuring the degree of cure or solidification of a composition. Desirably, such methods are quantitative and ascertain the degree of cure or solidification in a non-destructive manner such that they are adaptable for on-line, real-time monitoring.

18 Claims, 6 Drawing Sheets

METHODS FOR MEASURING DEGREE OF CURE OR SOLIDIFICATION OF A COMPOSITION

FIELD OF THE INVENTION

The present invention provides methods for measuring the degree of polymerization (cure) or solidification of a composition. Desirably, such methods are quantitative and ascertain the degree of polymerization (cure) or solidification in a non-destructive manner. Furthermore, such methods are adaptable for on-line, real-time monitoring.

BACKGROUND OF THE INVENTION

Several methods have been used for determining the relative degree of polymerization of photocure materials. Although these methods yield quantitative results, they do not provide any direct insight to the ultimate degree of conversion obtained. Furthermore, most of these methods employ destructive testing of bonded assemblies. With the increase of technological and customer demands, there is a need to measure adhesive cure during the production process to assure that the quality of the bond fits within the performance specifications of a given device. Although analytical methods are available for determining the conversion of photocurable systems, most of these analytical methods are difficult if not impossible to adapt for on-line, real-time monitoring. Thus, there is a need for quantitative methods for determining the degree of polymerization (cure) or solidification of a composition that is non-destructive, efficient and adaptable for on-line, real-time monitoring.

SUMMARY OF INVENTION

The present invention provides methods of quantitatively determining the degree of polymerization (cure) or solidification of a composition in a non-destructive manner. Advantageously, the degree of polymerization (cure) or solidification can be monitored in a reliable and simple manner using miniature, low cost, portable instrumentation that is readily adaptable for on-line, real-time use. Additionally, the degree of polymerization (cure) or solidification determined using the methods in accordance with the present invention correlate to that based on other analytical techniques. Likewise, the degree of polymerization (cure) or solidification can be correlated to a property or characteristic, such as pull strength or biocompatibility (e.g., cytotoxicity).

In one aspect of the invention, there is provided methods of measuring the degree of cure of a polymerizable composition having:

(i) mixing a wavelength-shift fluorophore with the polymerizable composition;

(ii) permitting polymerization of the polymerizable composition;

(iii) measuring fluorescence intensity at two emission wavelengths, one on each side of peak fluorescence intensity, of the wavelength-shift fluorophore and determining a ratio therefrom; and (iv) comparing the ratio to one or more reference value(s) that correlates the ratio to a known degree of polymerization of the polymerizable composition.

In one embodiment, the two emission wavelengths are near or at the minimum and maximum emission wavelengths of the wavelength-shift fluorophore.

In one embodiment, the wavelength-shift fluorophore comprises a dialkylamino group attached by a single bond to an aromatic group.

In one embodiment, the wavelength-shift fluorophore absorbs light in the visible light wavelength range. In one embodiment, the wavelength-shift fluorophore absorbs light in the ultraviolet light wavelength range.

In one embodiment, the wavelength-shift fluorophore is acrindine orange base, 4-dimethylamino-4-nitrostilbene, pyridine 1,2-(4-(4-dimethylaminophenyl)-1,3-butadiene)-3-ethylbenzothiazolium-p-toluenesulfonate, phenosafranin, methyl violet, 1-dimethylaminonapthalene-5-sulfonyl-n-chloride, diphenyl hexatriene, 1-dimethylaminonapthalene-5-sulfonyl-n-dibutylamide, 7-diethylamino-4-methyl-coumarin, or a combination of two or more thereof.

In one embodiment, the polymerizable composition comprises a (meth)acrylate, a urethane, a polyester, a silicone, a polyolefin, an epoxy, or a combination of two or more thereof in either a mixture or copolymer.

In one embodiment, one or more reference value(s) is obtained by Fourier transform infrared spectroscopy double bond conversion. In one embodiment, one or more reference value(s) is a strength property or biocompatibility characteristic.

In one embodiment, the polymerizable composition is light cured.

In one embodiment, one or more reference value(s) is in the form of a graph. In one embodiment, the reference value is a control standard for the wavelength-shift fluorophore.

In another aspect of the invention, there is provided methods of measuring the degree of solidification of a thermoplastic composition comprising:

(i) mixing a wavelength-shift fluorophore with the thermoplastic composition;

(ii) permitting solidification of the thermoplastic composition;

(iii) measuring fluorescence intensity at two emission wavelengths, one on each side of peak fluorescence intensity, of the wavelength-shift fluorophore and determining a ratio therefrom; and (iv) comparing the ratio to one or more reference value(s) that correlates the ratio to a known degree of solidification of the thermoplastic composition.

In one embodiment, the wavelength-shift fluorophore is acrindine orange base, 4-dimethylamino-4-nitrostilbene, pyridine I, 2-(4-(4-dimethylaminophenyl)-1,3-butadiene)-3-ethylbenzothiazolium-p-toluenesulfonate, phenosafranin, methyl violet, 1-dimethylaminonapthalene-5-sulfonyl-n-chloride, diphenyl hexatriene, 1-dimethylaminonapthalene-5-sulfonyl-n-dibutylamide, 7-diethylamino-4-methyl-coumarin, or a combination of two or more thereof.

In yet another aspect of the present invention, there is provided systems for non-destructively determining the degree of polymerization of a polymerizable composition or solidification of a thermoplastic composition comprising:

(i) a detection apparatus configured to detect fluorescence intensity of a wavelength-shift fluorophore present in the polymerizable composition or thermoplastic composition wherein the wavelength-shift fluorophore is exited by an excitation source;

(ii) an analyzer configured to determine a ratio of fluorescence intensity based on fluorescence intensity at two emission wavelengths, one on each side of peak fluorescence intensity, of the wavelength-shift fluorophore; and (iii) a correlating device configured to correlate the ratio with the degree of polymerization of the polymerizable composition or solidification of the thermoplastic composition.

In one embodiment, the system further comprises an excitation source configured to emit one or more light wavelengths capable of exciting the wavelength-shift fluorophore.

In one embodiment, wherein the detection apparatus measures fluorescence intensity at two emission wavelengths, one on each side of peak fluorescence intensity, of the wavelength-shift fluorophore.

In one embodiment, the system further comprises a communication interface configured to communicate the degree of polymerization to an external device.

In one embodiment, the system further comprises one or more reference value(s) that correlate the ratio with the degree of polymerization of the polymerizable composition or solidification of the thermoplastic composition.

DETAILED DESCRIPTION

Figure 1:
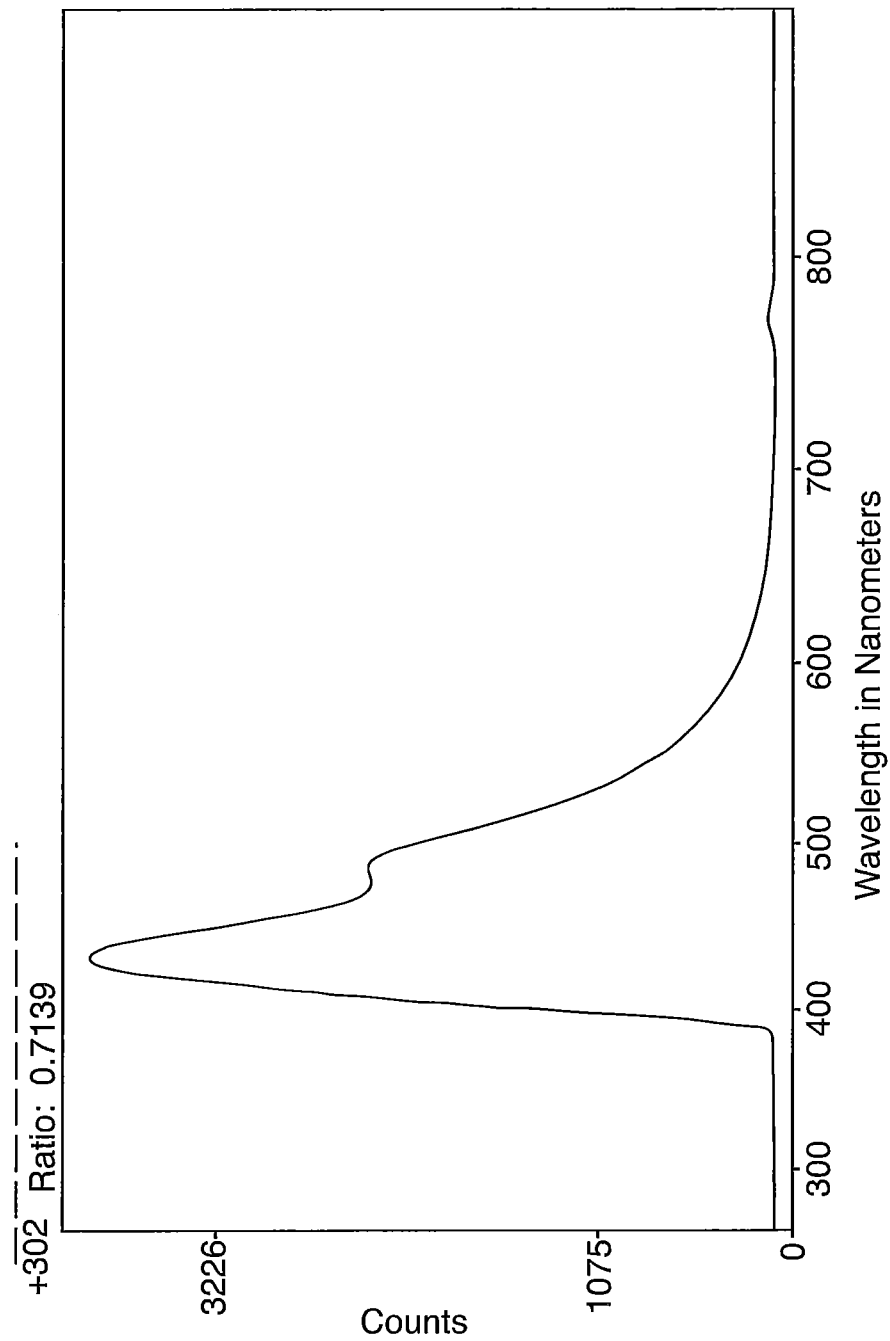
FIG. 1 is a graph of the fluorescence spectra of an exemplary polymerizable composition (Loctite® AssureCure™ 3924AC™ containing the wavelength-shift fluorophore 7-diethylamino-4-methyl-coumarin in an amount of 0.075% weight therein) following exposure to an excitation wavelength of 385 nm (filtered). Notably, the ratio of fluorescence intensity was determined to be 0.7139 based on the fluorescence intensity at 410 nm versus 444 nm. The integration time to reach a wavelength of 444.75 nm was 252 ms at which point the number of counts was 3532.

The methods and systems provided herein are useful in monitoring the degree of polymerization (cure) in a polymerizable composition or the degree of solidification of a thermoplastic composition. Such methods and systems are particularly useful to assure quality control in the manufacture of structural adhesives as well as biomedical applications.

In accordance with the present invention, fluorescence probe spectroscopy is employed whereby a shift in fluorescence emission wavelength of a fluorescent probe is correlated to the degree of cure, solidification or another property of the composition with which the fluorescent probe is combined. In one aspect, a ratio of fluorescence intensity is determined based on the fluorescence intensity at two emission wavelengths, one on each side of peak fluorescence intensity, of the wavelength-shift fluorophore which is then correlated to one or more reference values indicative of a degree polymerization (cure) in the case of a polymerizable composition or solidification in the case of a thermoplastic composition. Advantageously, this ratio acts as an internal standard and is independent of other variables including light intensity (for photocurable compositions) and coating thickness. Accordingly, a specific calibration need only be established once for each probe, formulation system and application. Furthermore, the blue-shift in emission wavelength combined with a reduction in fluorescence intensity of the wavelength-shift fluorophore can be monitored on-line using low cost, portable UV/V spectrometers. The methods of the present invention are thereby amenable for providing real-time monitoring to assure quality control during production.

Reference values for a given system are based on the generation of a correlation curve between the ratio of fluorescence intensity at two emission wavelengths, one on each side of peak fluorescence intensity, of a wavelength-shift fluorophore and the degree of polymerization measured using another analytical technique such as FTIR double bond conversion or one or more properties or characteristics (such as pull strength or biocompatibility). Such reference values need only be generated once for a particular composition. Reference values may be stored in a correlating device, such as a software program, which may be employed to ascertain the degree of polymerization for such a composition at a later time based solely on the ratio of fluorescence intensity at two emission wavelengths, one on each side of peak fluorescence intensity, of a wavelength-shift fluorophore.

Similarly, reference values may be generated for a thermoplastic composition that correlate the degree of solidification based on a quantitative property and the ratio of fluorescence intensity at two emission wavelengths, one on each side of peak fluorescence intensity, of a wavelength-shift fluorophore. Such reference values can be stored in a correlating device, such as a software program, which may be employed to ascertain the degree of polymerization for such a composition at a later time based solely on the ratio of fluorescence intensity at two emission wavelengths, one on each side of peak fluorescence intensity, of a wavelength-shift fluorophore.

As used herein, the phrase "wavelength-shift fluorophore" refers to a fluorescent compound which undergoes a photochromic shift. In particular, when excited by a suitable wavelength, the wavelength-shift fluorophore fluoresces at a first emission wavelength which under certain conditions shifts to a second emission wavelength. This photochromic shift is possible because the wavelength-shift fluorophore can exist in energetically different conformations, the relative concentrations of which are dependent on the surrounding microenvironment.

Wavelength-shift fluorophore include twisted intramolecular charge transfer (TICT) probes. In particular, such probes possess a dialkylamino substituent attached by a single bond to an aromatic ring. Free rotation around the single bond is believed to be important to the mechanism by which such TICT probes function. At a lower (unexcited) energy level, the aromatic ring and dialkylamino substituent form are believed to form a planar conformation. Upon excitation, the energy state increases and charge delocalization is established. To maximize charge separation the molecule rotates exploiting its free rotation potential resulting in the TICT excited state wherein the alkyl groups are perpendicular to the aromatic ring. Increased charge separation yield increased potential, lower energy transition at a longer wavelength.

Though not meant to be limited by any theory with the subject invention, the wavelength-shift fluorophore is believed to undergo a photochromatic shift when the microviscosity and micropolarity of the supporting medium in which it resides changes.

In the case of a polymerizable composition or thermoplastic having a wavelength-shift fluorophore such as a TICT probe, as the composition vitrifies, rotation of the probe is impeded and decay from the excited state occurs. Lower charge separation results in lower potential, higher energy (shorter wavelength) emission. (i.e., a blue shift). The second emission wavelength of the wavelength-shift fluorophore is shorter that the first emission wavelength (blue shift) and decreases in intensity. This shift, combined with reduction in peak intensity, can be used as an indicator of polymerization progress or thermoplastic solidification as the case may be.

Exemplary suitable wavelength-shift fluorophore include, but are not limited to, acrindine orange base, 4-dimethylamino-4-nitrostilbene, pyridine I, 2-(4-(4-dimethylaminophenyl)-1,3-butadiene)-3-ethylbenzothiazolium-p-toluenesulfonate, phenosafranin, methyl violet, 1-dimethylaminonapthalene-5-sulfonyl-n-chloride, diphenyl hexatriene, 1-dimethylaminonapthalene-5-sulfonyl-n-dibutylamide, 7-diethylamino-4-methyl-coumarin, or a combination of two or more thereof.

Generally, wavelength-shift fluorophore is added in small concentrations, typically <1% by weight of the total composition.

Suitable polymerizable compositions include, but are not limited to, curable compositions comprising a (meth)acrylate, a urethane, a polyester, a silicone, a polyolefin, an epoxy, or a combination of two or more thereof in either a mixture or copolymer.

Exemplary (meth)acrylates include a wide variety of materials represented by $H_2C=CGCO_2R$, where G may be hydrogen, halogen or alkyl of 1 to about 4 carbon atoms, and R may be selected from alkyl, cycloalkyl, alkenyl, cycloalkenyl, alkaryl, aralkyl or aryl groups of 1 to about 16 carbon atoms, any of which may be optionally substituted or interrupted as the case may be with silane, silicon, oxygen, halogen, carbonyl, hydroxyl, ester, carboxylic acid, urea, urethane, carbamate, amine, amide, sulfur, sulfonate, sulfone and the like.

Specific (meth)acrylates include polyethylene glycol di(meth)acrylates, desirably triethyleneglycol di(meth)acrylate, hydroxypropyl(meth)acrylate, bisphenol-A di(meth) acrylates, such as ethoxylated bisphenol-A (meth)acrylate ("EBIPA" OR "EBIPMA"), and tetrahydrofuran(meth)acrylates and di(meth)acrylates, citronellyl acrylate and citronellyl methacrylate, hexanediol di(meth)acrylate ("HDDA" or "HDDMA"), trimethylol propane tri(meth)acrylate, tetrahydrodicyclopentadienyl(meth)acrylate, ethoxylated trimethylol propane triacrylate ("ETTA"), triethylene glycol diacrylate and triethylene glycol dimethacrylate ("TRIEGMA").

In one embodiment, the polymerizable composition is light curable. Notably, photoinitiators enhance the rapidity of the curing process when the photocurable composition as a whole is exposed to electromagnetic radiation, such as actinic radiation. Desirably, the photoinitiator may be a non-peroxide photoinitiator, and most desirably may be a blend of propanone and phosphine oxide, however other photoinitiators may suitably be used. A photoinitiator may be added to the composition in an amount effective to respond to the electromagnetic radiation and to initiate and induce curing of the associated components, via substantial polymerization thereof.

Suitable photoinitiators useful with ultraviolet (UV) electromagnetic radiation curing mono- and polyolefinic monomers include free radical generating UV initiators such as substituted benzophenones and substituted acetophenones, benzoin and its' alkyl esters and xanthone and substituted xanthones. Preferred photoinitiators include diethoxy-acetophenone, benzoin methyl ether, benzoin ethyl ether, benzoin isopropyl ether, diethoxyxanthone, chloro-thio-xanthone, azo-bisisobutyronitrile, N-methyl diethanol-amine-benzophenone and mixtures thereof. Suitable photoinitiators include, but are not limited to, photoinitiators available commercially from Ciba Specialty Chemicals, under the "IRGACURE" and "DAROCUR" trade names, specifically IRGACURE 184 (1-hydroxycyclohexyl phenyl ketone), 907 (2-methyl-1-[4-(methylthio)phenyl]-2-morpholino propan-1-one), 369 (2-benzyl-2-N,N-dimethylamino-1-(4-morpholinophenyl)-1-butanone), 500 (the combination of 1-hydroxy cyclohexyl phenyl ketone and benzophenone), 651 (2,2-dimethoxy-2-phenyl acetophenone), 1700 (the combination of bis(2,6-dimethoxybenzoyl-2,4,4-trimethyl pentyl) phosphine oxide and 2-hydroxy-2-methyl-1-phenyl-propan-1-one), 819 [bis(2,4,6-trimethyl benzoyl)phenyl phosphine oxide], 2022 [IRGACURE 819 dissolved in DAROCUR 1173 (described below)] and DAROCUR 1173 (2-hydroxy-2-methyl-1-phenyl-1-propan-1-one) and 4265 (the combination of 2,4,6-trimethylbenzoyldiphenyl-phosphine oxide and 2-hydroxy-2-methyl-1-phenyl-propan-1-one); and the visible light [blue] photoinitiators, dl-camphorquinone and IRGACURE 784DC. Furthermore, combinations of two or more photoinitiators may also be employed.

Additional suitable photoinitiators include alkyl pyruvates, such as methyl, ethyl, propyl, and butyl pyruvates, and aryl pyruvates, such as phenyl, benzyl, and appropriately substituted derivatives thereof.

Thermoplastic compositions suitable useful for use in the present invention include, but are not limited to, polycarbonate acrylate, silicone, polyisobutylene, and combinations of two or more thereof.

Suitable detection apparatus include, but are not limited to, spectrophotometers.

A suitable analyzer includes, but is not limited to, a software program that has a feature which calculates a ratio of fluorescence intensity based on fluorescence intensity at two emission wavelengths, one on each side of peak fluorescence intensity, of a wavelength-shift fluorophore used in a given system.

Suitable excitation source include, but are not limited to, fiber optic excitation source such as Loctite® CureJet LED Systems.

The invention may be further understood with reference to the following non-limiting examples.

EXAMPLES

In accordance with the present invention, exemplary polymerizable compositions having a wavelength-shift fluorophore therein were subjected to polymerization during which time the emission wavelengths of the wavelength-shift fluorophore were measured and correlated to the degree of polymerization or another polymer property.

In particular, the exemplary polymerizable composition, Loctite® AssureCure™ 3924AC™ having a wavelength-shift fluorophore (i.e., 7-diethylamino-4-methyl-coumarin) in an amount of 0.075% weight therein, was subjected to polymerization via light curing and the florescence spectra of the wavelength-shift fluorophore detected.

As illustrated in FIG. 1, following exposure to an excitation wavelength of 385 nm (filtered), there was a shift in fluorescence emission wavelength as well as a reduction in fluorescence peak intensity of the wavelength-shift fluorophore. Notably, the fluorescence intensity ratio was determined to be 0.7139 at 410/444 nm.

Likewise, polymerization via light curing was examined using different three part geometries (namely needles, tubesets and lapshears). Surprisingly, despite the different geometries, no significant difference in the fluorescence intensity ratio was detected. Thus, the fluorescence intensity ratio acts as an internal standard which is independent of the geometry of the polymerizing composition.

Figure 2:
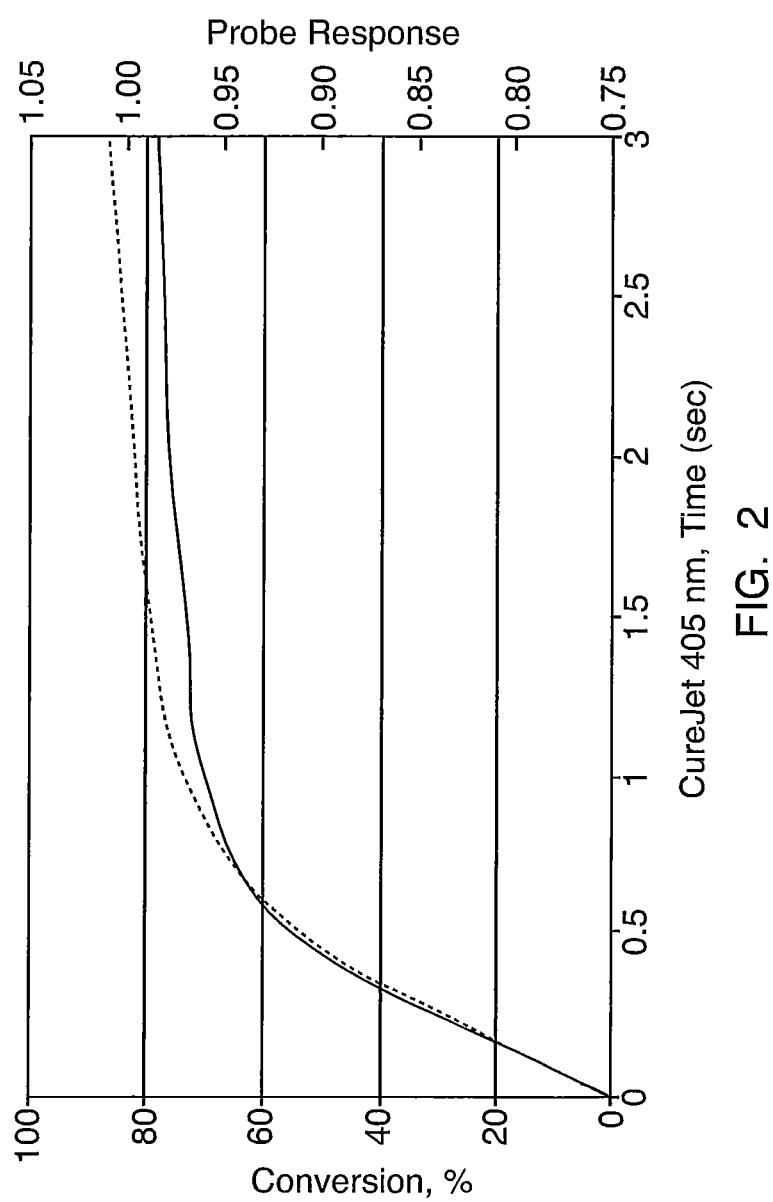
FIG. 2 is a graph of the correlation curve for an exemplary polymerizable composition (Loctite® AssureCure™ 3924AC™ containing the wavelength-shift fluorophore 7-diethylamino-4-methyl-coumarin in an amount of 0.075% weight therein) wherein the composition is polymerized in a BD Eclipse-Opaque Hub (NP). In particular, the % conversion (solid line) and probe response (dashed line) is depicted over a period of 3 seconds of exposure to CureJet 405 nm.
Figure 3:
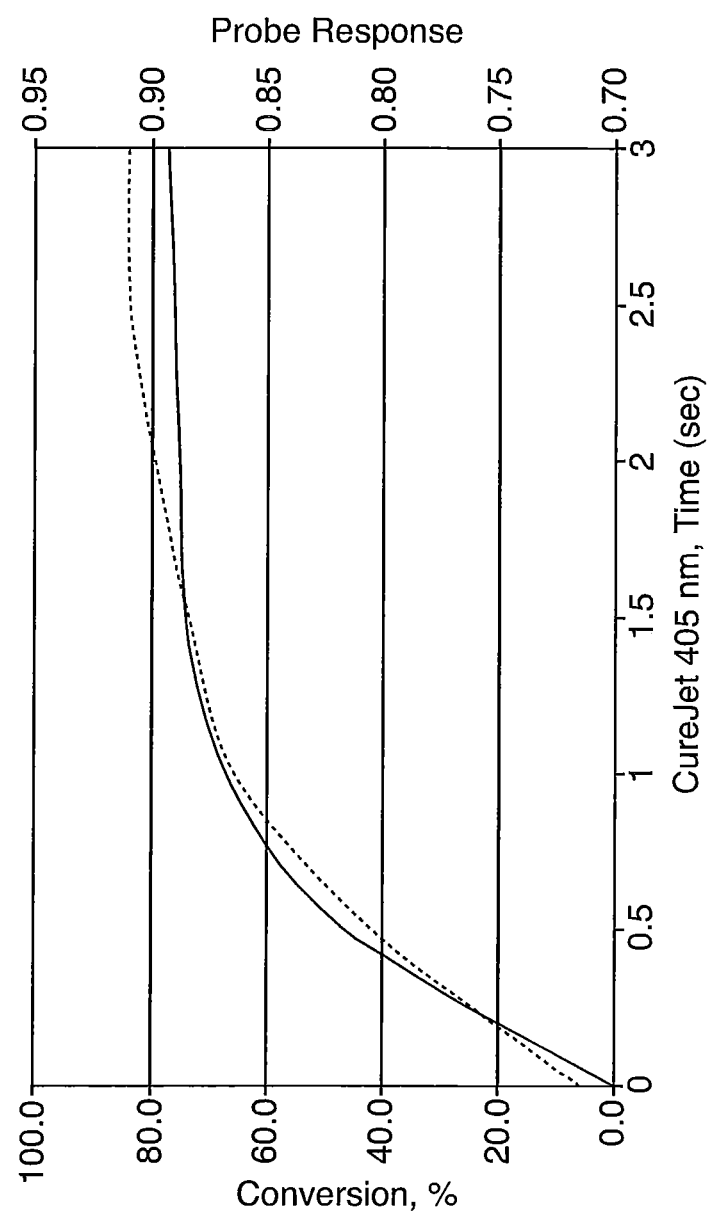
FIG. 3 is a graph of the correlation curve for an exemplary polymerizable composition (Loctite® AssureCure™ 3924AC™ containing the wavelength-shift fluorophore 7-diethylamino-4-methyl-coumarin in an amount of 0.075% weight therein) wherein the composition is polymerized in a BD Eclipse-Clear Hub (IV). In particular, the % conversion (solid line) and probe response (dashed line) is depicted over a period of 3 seconds of exposure to CureJet 405 nm.
Figure 4:
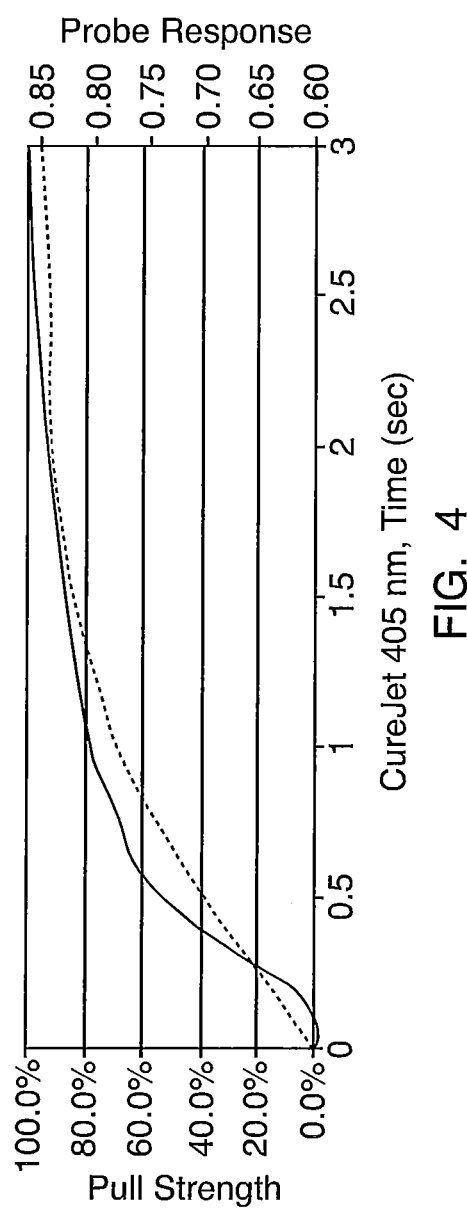
FIG. 4 is a graph of the correlation curve for an exemplary polymerizable composition (Loctite® AssureCure™ 3924AC™ containing the wavelength-shift fluorophore 7-diethylamino-4-methyl-coumarin in an amount of 0.075% weight therein) wherein the composition is polymerized in a 3924-PC Hub/SS Cannula. In particular, the pull strength (solid line) and probe response (dashed line) is depicted over a period of 3 seconds of exposure to CureJet 405 nm.
Figure 5:
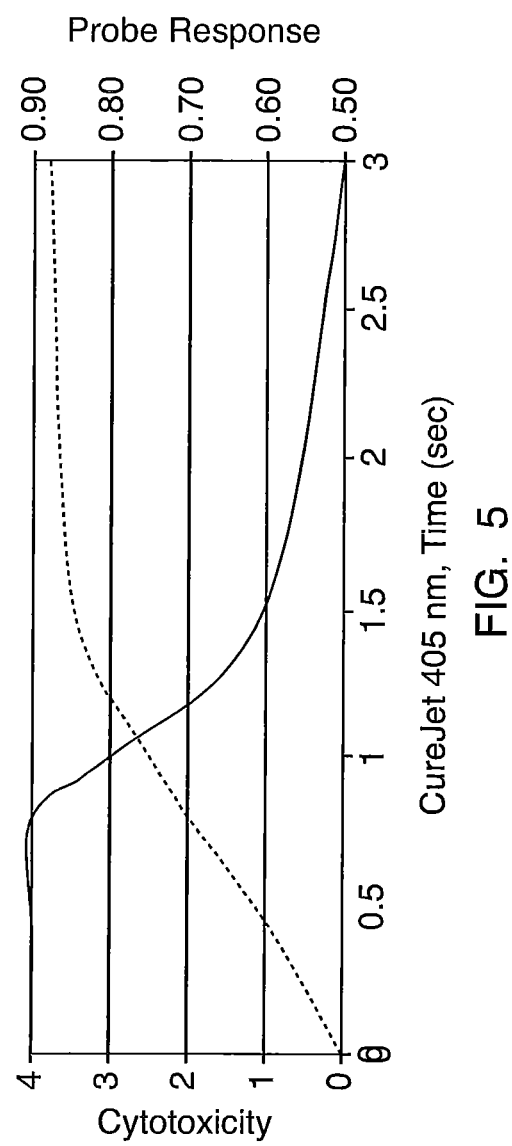
FIG. 5 is a graph of the correlation curve for an exemplary polymerizable composition (Loctite® AssureCure™ 3924AC™ containing the wavelength-shift fluorophore 7-diethylamino-4-methyl-coumarin in an amount of 0.075% weight therein) wherein the composition is polymerized in a 3924-PC laps. In particular, the cytotoxicity (solid line) and probe response (dashed line) is depicted over a period of 3 seconds of exposure to CureJet 405 nm.

Additionally, excellent correlation between probe response and polymerization (cure) was attained in light cure systems using measures of polymerization (cure) including FTIR double bond conversion (as illustrated in FIGS. 2 and 3), performance properties including pull strength (as illustrated in FIG. 4) and biocompatibility compliance including cytotoxicity (as illustrated in FIG. 5).

Notably, the correlation curves provided in FIGS. 2-5 can be used as reference values to correlate the degree of polymerization of Loctite® AssureCure™ 3924AC™ having the wavelength-shift fluorophore 7-diethylamino-4-methyl-coumarin therein based solely on the ratio of fluorescence intensity for such a system undergoing polymerization at a later time.

Figure 6:
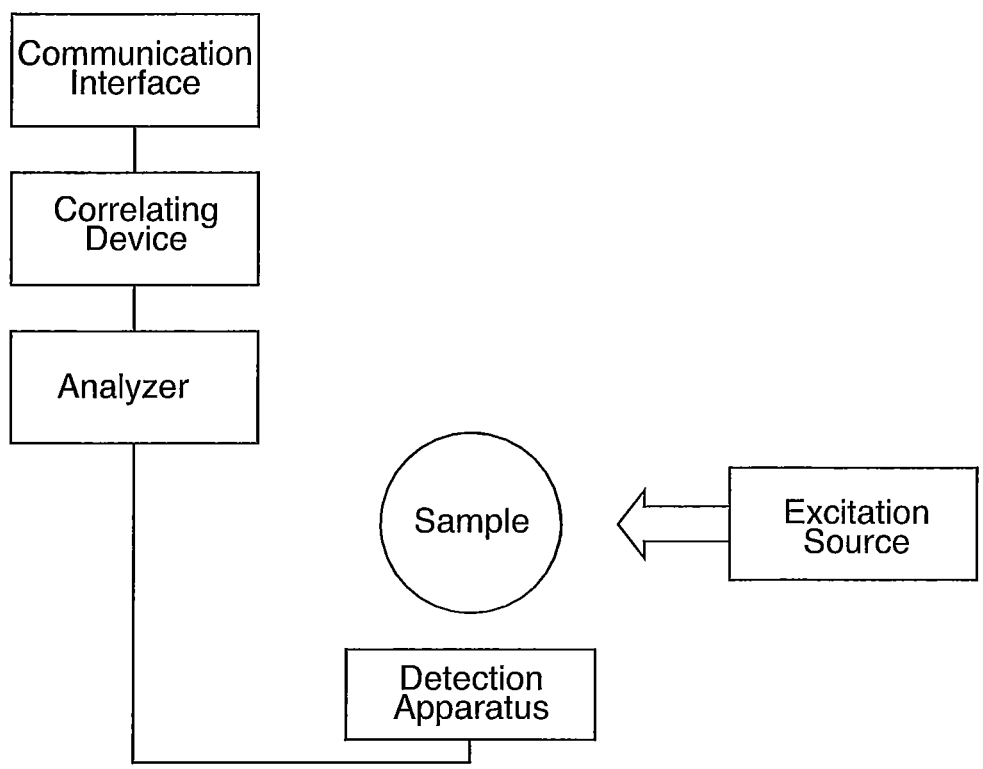
FIG. 6 shows a diagram of a system suitable for use in conjunction with the present invention.

An illustrative diagram of a system suitable for use with the present invention is shown in FIG. 6. In brief, the sample composition is subjected to an excitation source and a detection apparatus (having at least one detection site) measures fluorescence intensity at two emission wavelengths, one on each side of peak fluorescence intensity, of the wavelength-shift fluorophore. An analyzer calculates a ratio of fluorescence intensity based on fluorescence intensity at two emission wavelengths, one on each side of peak fluorescence intensity, of the wavelength-shift fluorophore. A correlating device having one or more reference value(s) stored therein, correlates the ratio of fluorescence intensity with the degree of polymerization of the polymerizable composition or solidification of the thermoplastic composition.

What is claimed is:

1. A method of measuring the degree of polymerization of a polymerizable adhesive composition comprising:
    (i) mixing a wavelength-shift fluorophore comprising 7-diethylamino-4-methyl -coumarin with the polymerizable adhesive composition;
    (ii) applying the polymerizable adhesive composition to substrates to be bonded to form a bondable assembly;
    (iii) permitting polymerization of the polymerizable adhesive composition to bond the substrates to be bonded to form a bonded assembly;
    (iv) measuring fluorescence intensity at two emission wavelengths, one on each side of peak fluorescence intensity of the wavelength-shift fluorophore, and determining a ratio therefrom; and
    (v) comparing the ratio to predetermined reference values that correlate the ratio of peak fluorescence intensity to
        (a) a known degree of polymerization of the polymerizable adhesive composition obtained through measurements of the degree of polymerization of the polymerizable adhesive composition and/or (b) a known degree of performance properties of the polymerizable adhesive composition obtained through measurements of the performance properties of the polymerizable adhesive composition.

2. The method of claim 1, wherein the two emission wavelengths are near or at the minimum and maximum emission wavelengths of the wavelength-shift fluorophore.

3. The method of claim 1, wherein step (iv) and step (iv) are performed more than once as the polymerizable adhesive composition undergoes polymerization.

4. The method of claim 1, wherein the polymerizable composition comprises a (meth)acrylate, a urethane, a polyester, a silicone, a polyolefin, an epoxy, or a combination of two or more thereof in either a mixture or copolymer.

5. The method of claim 1, wherein one or more reference value(s) is obtained by Fourier transform infrared spectroscopy double bond conversion.

6. The method of claim 1, wherein one or more reference value(s) is a strength property or biocompatibility characteristic.

7. The method of claim 1, wherein one or more reference value(s) is in the form of a graph.

8. The method of claim 1, wherein the reference value is a control standard for the wavelength-shift fluorophore.

9. A method of measuring the degree of solidification of a thermoplastic adhesive composition comprising:
    (i) mixing a wavelength-shift fluorophore comprising 7-diethylamino-4-methyl -coumarin with the thermoplastic adhesive composition;
    (ii) permitting solidification of the thermoplastic adhesive composition;
    (ii) measuring fluorescence intensity at two emission wavelengths, one on each side of peak fluorescence intensity, of the wavelength-shift fluorophore and determining a ratio therefrom; and
    (iv) comparing the ratio to one or more reference value(s) that correlates the ratio to a known degree of solidification of the thermoplastic adhesive composition.

10. A system for non-destructively determining the degree of polymerization of a polymerizable adhesive composition or solidification of a thermoplastic adhesive composition comprising:
    (i) a detection apparatus configured to detect fluorescence intensity of a wavelength-shift fluorophore present in the polymerizable adhesive composition or thermoplastic adhesive composition wherein the wavelength-shift fluorophore is exited by an excitation source and wherein the fluorophore is a fluorophore comprising 7-diethylamino-4-methyl-coumarin;
    (ii) an analyzer configured to determine a ratio of fluorescence intensity based on fluorescence intensity at two emission wavelengths, one on each side of peak fluorescence intensity, of the wavelength-shift fluorophore; and
    (iii) a correlating device configured to correlate the ratio with the degree of polymerization of the polymerizable composition or solidification of the thermoplastic adhesive composition.

11. The system of claim 10, further comprising an excitation source configured to emit one or more light wavelengths capable of exciting the wavelength-shift fluorophore.

12. The system of claim 10, wherein the detection apparatus measures fluorescence intensity at two emission wavelengths, one on each side of peak fluorescence intensity, of the wavelength-shift fluorophore.

13. The system of claim 10, further comprising a communication interface configured to communicate the degree of polymerization to an external device.

14. The system of claim 10, further comprising one or more reference value(s) that correlate the ratio with the degree of polymerization of the polymerizable composition or solidification of the thermoplastic adhesive composition.

15. The method of claim 1, wherein the substrates are each constructed from polycarbonate.

16. The method of claim 1, wherein one of the substrates is constructed from polycarbonate and the other substrate is constructed from stainless steel.

17. The method of claim 1, wherein one of the substrates is a cannula and the other substrate is a needle.

18. The method of claim 1, wherein step (iii) occurs after exposure of the bondable assembly to actinic radiation.

* * * * *